United States Patent [19]

Shin

[11] Patent Number: 4,692,555

[45] Date of Patent: Sep. 8, 1987

[54] PREPARATION OF DIPHENOLICS

[75] Inventor: Kju H. Shin, Baton Rouge, La.

[73] Assignee: Ethyl Corporation, Richmond, Va.

[21] Appl. No.: 598,225

[22] Filed: Apr. 9, 1984

[51] Int. Cl.$^4$ ........................ C07C 39/12; C07C 37/11
[52] U.S. Cl. .................................... 568/722; 568/723; 568/727
[58] Field of Search ................ 568/716, 727, 722, 723

[56] References Cited

U.S. PATENT DOCUMENTS

| | | | |
|---|---|---|---|
| 2,838,571 | 6/1958 | Filbey | 568/662 |
| 2,839,586 | 6/1958 | Fritz | 568/722 |
| 2,841,623 | 7/1958 | Norton et al. | 568/662 |
| 2,841,624 | 7/1958 | Norton et al. | 568/662 |
| 3,053,803 | 9/1962 | Jaffe et al. | 568/722 |

OTHER PUBLICATIONS

Houben-Weyl, vol. 8, pp. 404-405 "Methoden de Organischem Chemie" (1951).
Reid et al., "J. American Chemical Society", vol. LXI, (1939).

Primary Examiner—Werren B. Lone
Attorney, Agent, or Firm—Donald L. Johnson; John F. Sieberth; J. D. Odenweller

[57] ABSTRACT

A process for the production of diphenolic compounds having a divalent bridge. A first disubstituted phenol is reacted with an aldehyde in the presence of a secondary amine and excess alcohol to form an ether intermediate. The ether intermediate is reacted with a phenol having an open ortho or para position to form a diphenolic.

25 Claims, No Drawings

PREPARATION OF DIPHENOLICS

BACKGROUND OF THE INVENTION

1. Field of the Invention

The present invention is related to processes for the preparation of diaromatic compounds having a divalent bridging group and in particular to processes for the synthesis of diphenolic compounds.

2. Description of the Prior Art

Certain unsymmetrical diphenolic compounds have been formed according to processes of the prior art. However, these compounds have only been prepared by lengthy routes and require the presence of at least one t-butyl group on one of the phenolic moieties of the product compound.

There exists a need for a process to provide selectively ortho and para substituted diphenolic compounds having a divalent bridge between the two phenolic moieties.

CROSS-REFERENCE

Reference is made to copending application Ser. No. 598,058, filed April 9 to Shin and Tatum and to copending application Ser. No. 450,207 to Mina filed Dec. 16, 1982. Those applications are commonly assigned with the present application.

SUMMARY OF THE INVENTION

The present invention is directed to a process for the preparation of (optionally) unsymmetrical diphenolic compounds which are bridged by a divalent radical. Such diphenolic compounds have many utilities such as an additive antioxidant or a curing agent for polyurethanes or epoxies. The present invention is a process for preparation of diphenolic compounds, said process comprising:

(1) reacting in the presence of a secondary amine an aldehyde, an alcohol, and a first phenol having exactly two of the three positions ortho and para to the hydroxyl group substituted and the other two positions optionally substituted with independently selected alkyl, cycloalkyl, aryl, alkaryl, aralkyl, halogen, or a group of the formula —(R'''')$_n$—CX$_3$ where R'''' is a divalent hydrocarbon preferably containing about one to twelve carbon atoms, n is zero or one, and X is halogen; and (2) reacting the ether product of step (1) in the presence of an acid catalyst with a second phenol having at least one position ortho or para to the hydroxyl group unsubstituted except for H.

The present invention is a process for the production of divalent-hydrocarbon-bridged diphenolic compounds of structures I, II, III, or IV:

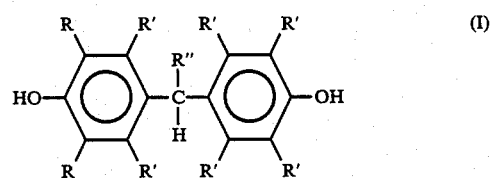
(I)

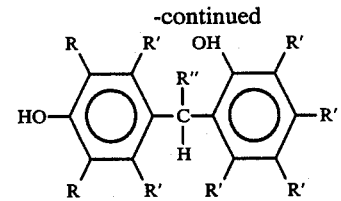
(II)

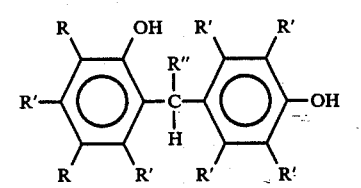
(III)

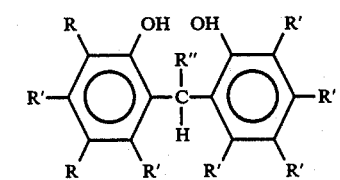
(IV)

wherein the R are independently selected from the group consisting of alkyl, cycloalkyl, aromatic, halogen, or a group of the formula —(R'')$_n$—CX$_3$ wherein R'' is a divalent hydrocarbon preferably of 1–12 carbon atoms, n is 0 or 1, and X is halogen; wherein the R' are independently selected from H and the same group as the R; and wherein R'' is selected from H or alkyl, cycloaliphatic, alkenyl, aromatic, heteroatomic, or heterocyclic radicals; said process comprising reacting a phenol of structure A or B:

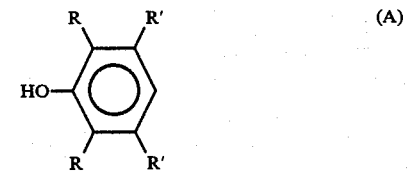
(A)

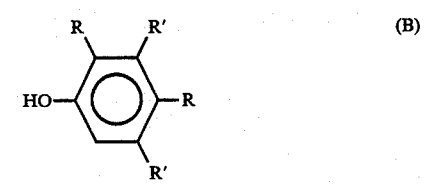
(B)

wherein the R and R' are as defined above, with an alcohol of structure R'''—OH wherein R''' is a monovalent hydrocarbon and an aldehyde of structure R''CHO wherein R'' is as defined above, in the presence of a secondary amine to form an ether intermediate of structure C or D:

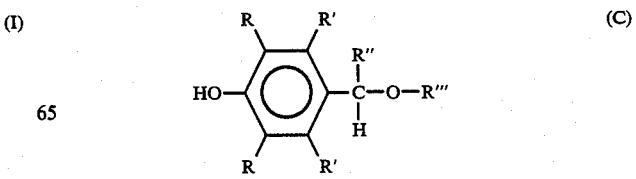
(C)

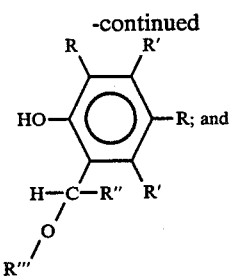

reacting said ether intermediate with a phenol of structure E or F:

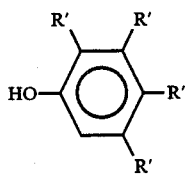

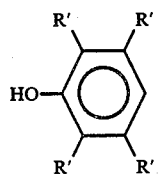

wherein the R' are as defined above, in the presence of an acid catalyst.

The present invention is also a process for the production of a carbon-bridged diphenolic compound, said process comprising reacting an ether of structure C or D

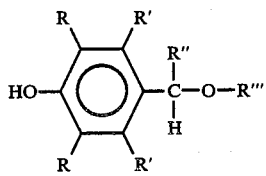

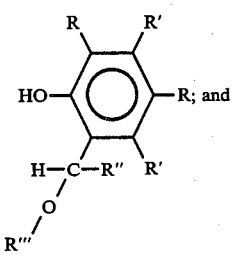

with a phenol which may or may not be ring-substituted provided that one position ortho to the hydroxyl group is unsubstituted except for H in the presence of an acid catalyst.

DESCRIPTION OF THE PREFERRED EMBODIMENT

According to the present invention, various (optionally) unsymmetrical diphenolic compounds are provided by a novel process which results in a relatively discoloration free product in excellent yields.

The present invention is a two step process for the preparation of diphenolics. The first step uses a first phenol having at least two substituents, one of said at least two substituents being in a position ortho to the hydroxyl function and the other of said at least two substituents being in either the ortho or para position to the hydroxyl function.

According to the invention a first phenol which is at least disubstituted, an alcohol, and an aldehyde are reacted in the presence of a catalytic portion of a secondary amine. In a second step of the inventive process, the resulting ether is reacted with a second phenol which is at least disubstituted.

A first phenol is disubstituted in exactly two of the three positions ortho and para to the hydroxyl group of the phenol. The second phenol may be the same as the first phenol and has at least one position ortho or para to the hydroxyl group unsubstituted except for H. The other two (meta) positions of the phenols are optionally substituted as indicated below. Thus, the first phenol of the invention includes those having 2–4 ring substituents, preferably 2 only, that may be the same or different, preferably the same. The second phenol of the invention may have 0–4 ring substituents. The substituents of the phenols may be of any size, length, or degree of branching so long as the reactants may be combined to carry out the first step of the invention. In this regard, the substituents may be required to be of such a size or shape as to permit solubility in a solvent or other reactant. The first phenol of the invention can be represented by the structures

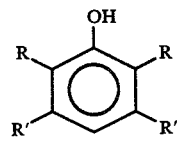

or

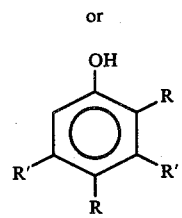

wherein the R are the same or different and are selected from the group consisting of halogen, alkyl (preferably containing 1–20 carbon atoms), cycloalkyl (preferably containing 5–8 carbon atoms), aromatics (preferably containing 6–12 carbon atoms), and groups having the formula $-(R'''')_n-CX_3$ wherein $R''''$ is a divalent hydrocarbon group containing 1–12 carbon atoms, n is 0 or 1, and X is halogen (preferably chlorine or bromine) and the R' are selected from hydrogen and the same groups as R.

According to the present invention, in a first step, one of the above described phenolics of structure IV is reacted in the presence of a catalytic portion of a secondary amine to form an ether intermediate. That is, benzylic type ethers are formed when formaldehyde and an alcohol are reacted with the starting phenol. Similarly, various other ethers may be formed and a radical of the aldehyde becomes substituted between a radical of the alcohol and the phenol to form a compound having one of the following general structures C and D:

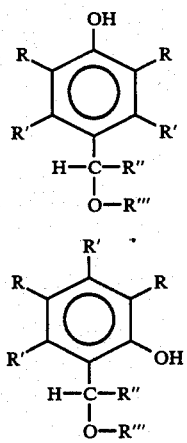

wherein R, R', and R" are as defined above and R'" is a hydrocarbon radical from the alcohol reactant R'"OH and R'" is preferably alkyl, cycloalkyl, or aromatic.

Representative examples of the first phenols include:
2,6-dimethylphenol
2,6-diisopropylphenol
2,3,6-trimethylphenol
2-methyl-6-tert-butylphenol
2,3,5,6-tetramethylphenol
2-methyl-6-sec-dodecylphenol
2-methyl-6-sec-eicosylphenol
2-methyl-6-cyclohexylphenol
2,6-dicyclopentylphenol
2-ethyl-6-cyclooctylphenol
2,6-diethylphenol
2-methyl-6-ethylphenol
2-ethyl-6-isopropylphenol
2-ethyl-6-chlorophenol
2-methyl-6-fluorophenol
2-methyl-6-phenylphenol
2-ethyl-6-benzylphenol
2,6-di-(α-methylbenzyl)phenol
2-methyl-6-(trichloromethyl)phenol
2-isopropyl-6-(2,2,2-trichloroethyl)phenol
2-isopropyl-6-(2-trichloromethylbutyl)phenol
2,3-dimethyl-6-(trichloromethyl)phenol
2,6-diisopropyl-3-(2-tribromoethyl)phenol
2-tert-butyl-6-(tribromomethyl)phenol
2,4-dimethylphenol
2,4-diethylphenol
2,4-diisopropylphenol
2-methyl-4-cyclohexylphenol
2-tert-butyl-4-(tribromomethyl)phenol
2-sec-eicosyl-3,4-dimethylphenol
and the like.

The preferred phenols are the 2,4- and 2,6-di-lower alkylphenols such as:
2,4-dimethylphenol
2,4-diethylphenol
2,4-diisopropylphenol
2,6-dimethylphenol
2,6-diethylphenol
2,6-diisopropylphenol
2-methyl-4-isopropylphenol
2-methyl-6-ethylphenol
2-ethyl-6-isopropylphenol
and the like. Still more preferably the R are methyl, ethyl, or isopropyl groups.

The second phenols of the invention may be the same as the first or may be substituted by the same R' groups as the first phenol in any of the ring positions so long as one ortho or para position is unsubstituted (except by H). Thus the following phenols are also usable as the second phenol of the invention (in the second step thereof):
phenol
orthocresol
metacresol
ortho-ethylphenol
ortho-isopropylphenol
ortho-tert-butylphenol
ortho-sec-butylphenol
ortho-isobutylphenol
ortho-cyclopentylphenol
ortho-cyclohexylphenol
ortho-heptylphenol
meta-ethylphenol
meta-isopropylphenol
meta-tert-butylphenol
meta-sec-butylphenol
meta-isobutylphenol
meta-cyclopentylphenol
meta-cyclohexylphenol
meta-tert-amylphenol
meta-n-octylphenol
para-ethylphenol
para-isopropylphenol
para-n-heptylphenol
para-cyclopentylphenol
para-tert-butylphenol
ortho-chlorophenol
ortho-bromophenol
ortho-(trichloromethyl)phenol
2-chloro-4-ethylphenol
2-methyl-3-chloro-6-tert-butylphenol
2,3-difluorophenol
2-bromo-6-benzylphenol
2,5-diphenylphenol
2-methyl-6-phenylphenol
2-chloro-3,6-dicyclopentylphenol
and the like.

Substituents of 1–20 carbon atoms are preferred. Lower alkys are more preferred since they may ultimately serve as hindering groups of the diphenolic product. The 2,4- and 2,6-dialkylated phenols are most preferred for making the diphenolic products of the invention. Suitable substituents include: methyl, ethyl, isopropyl, t-butyl, sec-butyl, trichloromethyl, chlorine, bromine, trifluoromethyl, benzyl, phenyl, cyclopentyl, cyclohexyl, and the like.

Most secondary amines are suitable catalysts for the first step of the inventive reaction. The preferred secondary amines have the structure:

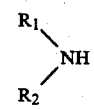

wherein $R_1$ and $R_2$ are alkyl, cycloalkyl, hydroxyalkyl, cycloalkanol, alkaryl, aralkyl, heterocyclic, or together with the nitrogen to which they are attached form a ring.

Representative examples of these secondary amines are dimethylamine, methylisobutylamine, diisobutylamine, methyltriacontylamine, dicyclohexylamine, methylcyclohexylamine, methylcyclopentylamine, methylcyclooctylamine, diethanolamine, methylethanolamine, methyl(2-hydroxybutyl)amine, methyl (2-hydroxycyclohexyl)amine, ethyl(4-hydroxycyclohexyl)amine, N-methylaniline, methyl-o-tolylamine, dibenzylamine, methylbenzylamine, methyl(α-methylbenzyl)amine, N-methyl-p-toluidine, N-[N-(3-aminopropyl)-morpholine]N-methylamine, piperidine, morpholine, piperazine and the like.

The dialkylamines and hydroxyalkylamines are more preferred since they are readily available, cheap, and form a catalyst species. Included are dimethylamine, diethylamine, dipropylamine, di-n-butylamine, diisoamylamine, methylethylamine, diisopropylamine, didodecylamine, methylisopropylamine and the like. Still more preferably $R_1$ and $R_2$ are lower alkyl groups containing 1-4 carbon atoms such as dimethylamine, diethylamine, methylethylamine, diisopropylamine, methylisobutylamine and the like. The most preferred dialkylamines are dimethylamine and diethylamine, especially dimethylamine.

Preferred hydroxyalkylamines are those in which the hydroxy alkyl groups contain about 2-4 carbon atoms such as diethanolamine, methylethanolamine, di-(2-hydroxypropyl)amine, di-(2-hydroxybutyl)amine, ethylethanolamine, isobutylethanolamine and the like. The most preferred hydroxyalkylamines are the di-(hydroxyalkyl)amines especially diethanolamine. Also suitable is methyl-N'-N'-diethylethylenediamine. Other usable secondary amines include piperidine, 1,2,3,4-tetrahydroisoquinoline, 6-methoxy-1,2,3,4-tetrahydroisoquinoline, morpholine, piperazine, α-methylaminopropiophenone, β-acetylethylbenzylamine, benzyl-(2-cyclohexanonylmethyl)-amine, and 3,4-methylenedioxybenzyl-(2-cyclohexanonylmethyl)amine. It is possible to use mixtures of the above or other secondary amines. When physiologically active materials are sought relatively more complex secondary amines may be used. The acid salts of secondary amines are also usable. These include the salts of HCl, acetic acid, nitric acid, propionic acid, benzoic acid, sulfuric acid, and the like.

Generally, a small amount of secondary amine is needed. The amount should be sufficient to form a catalytic species for the first step of the reaction. A suitable range is 0.05 to 0.5 mole secondary amine per mole of the first phenol. A preferred range is 0.05 to 0.1 mole secondary amine per mole of first phenol.

Most aldehydes are suitable for use according to the invention but those with twelve or fewer carbon atoms are more readily used to make the ethers of structure C or D. Those with eight or fewer carbon atoms are most preferred. The aldehydes usable with the invention include formaldehyde, acetaldehyde, butyraldehyde, benzaldehyde, benzylaldehyde, propionaldehyde, benzalacetaldehyde (cinnamaldehyde —($C_6H_5$)CH=CH—CHO), cuminicaldehyde (($CH_3$)$_2$CH($C_6H_4$)CHO or para-isopropylbenzaldehyde), heptylic aldehyde, furfuraldehyde, crotonaldehyde, and glyoxalic acid and its esters.

The phenolic groups of the compounds formed by the process of the invention are bonded to the same carbon atom which is part of the divalent radical bridge. That is the divalent radical from the aldehyde always bridges the phenolic moieties across a single carbon atom.

Accordingly, the divalent radicals which bridge the phenolic moieties include furfurylidene, propenylidene, benzylidene, β-phenethylidene (($C_6H_5$)$CH_2$CH), methylene, ethylidene, propylidene, butylidene, isobutyrilidene, cyclohexylmethylene, 2,2-dimethylpropylidene, propenylidene ($CH_2$=CH—CH), and the divalent radicals from glyoxalic acid and its esters such as

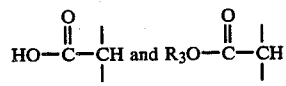

wherein the $R_3$ is a hydrocarbyl radical. The radical

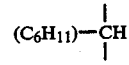

may be obtained by hydrogenation of benzaldehyde prior to use in the production of the ethers of structure II.

From the above it is clear that the R" of structures I–IV may, among other radicals, be alkyls such as methyl, ethyl, propyl, isopropyl, n-butyl, isobutyl, sec-butyl, n-hexyl, and the like; cycloaliphatics such as cyclohexyl or cyclopentyl; aromatics such as phenyl, benzyl or cumyl; heterocyclics such as the monovalent furan radical from fufurylidene; heteroatomics such as the radicals

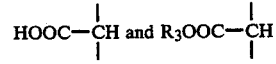

from glyoxalic acid and its esters; and alkenyls such as ethenyl, propenyl, and the like.

According to the first step of the inventive process, ethers are formed by reaction of the first phenol, aldehyde, and alcohol in the presence of a secondary amine (catalyst source). The alcohols suitable for the invention include the alkanols, cycloalkanols, aromatic alcohols and others including the following: methanol, ethanol, isopropanol, cyclohexanol, phenol, benyzl alcohol, and others.

The reactants may be combined in a broad range of amounts so as to produce an ether product from the first step of the inventive process. Preferably, the first phenol, aldehyde, and alcohol are provided in equal molar amounts so as to produce an ether of the above described type as the major product. However, the first step of the inventive process may be more readily carried out by using an excess of the alcohol reactant as a solvent or reaction medium.

According to the second step of the inventive process, the ether product as described above from the first step of the invention is reacted with a second phenol of the type described in the presence of an acid to produce a diphenolic compound bridged by a divalent group. Various acids are suitable to catalyze this reaction including the carboxylic and inorganic acids. The mineral acids are usable and sulfuric acid is most preferred. Also usable are phosphoric, acetic acid, formic acid, trichloroacetic acid, trifluoroacetic acid, benzene sulfonic acid, para-toluene sulfonic acid, or other alkyl sulfonic acids or haloalkyl sulfonic acids such as: methane sulfonic acid, methane disulfonic acid, ethane sulfonic acid, propane sulfonic acid, butane sulfonic acid, butane disulfonic acid, fluoromethane sulfonic acid, difluoromethane sulfonic acid, trifluoromethane sulfonic acid, trichloroethane sulfonic acid, trichloromethane sulfonic acid, perchloroethane sulfonic acid, tribromomethane sulfonic acid, 3,3,3-tribromopropane sulfonic acid, tris(trifluoromethyl) methane sulfonic acid, and the like. Only an amount of acid necessary to catalyze the reaction is required, although larger amounts may be used.

For the preferred range of strength of sulfuric acid (70-84%) a usable range of acid is 2.0 to 500 grams acid per mole of the ether intermediate. A preferred range is 150 to 300 grams acid per mole ether intermediate. For weaker acids, a higher range is required. Equal molar amounts of the ether product of the first step of the reaction and the second phenol are desired but an excess of one reactant may readily be used.

Concentrated sulfuric acid is very usable in conducting the reaction.

Various solvents may be used for the reaction of the ether product of the first step of the reaction with the second phenol. The solvents and other reaction mediums include methylene chloride which is most preferred. Other mediums include those that are substantially inert and have a normal boiling range from about 30° to about 100° C. An especially useful range is 30°-75° C. Higher boiling solvents can be used if the reaction is operated under sufficient vacuum to lower the boiling temperature of the mixture to the 30°-100° C. By "substantially inert" is meant that the solvents do not react to any extent with the other reactants used in the process under the reaction conditions. Preferred solvents are aliphatic hydrocarbons and chlorinated hydrocarbons. Examples of these are: pentane, hexane, isohexane, heptanes, 2,2,4-tri-methyl pentane ("isooctane"), and the like.

The preferred solvents are the chloroalkanes such as methylene chloride (dichloromethane), 1,1-dichloropropane, 1,2-dichloropropane, 2,2-dichloropropane, 1,1-dichloroethane, 1,2-dichloroethane, 1,1,1-trichloroethane, n-butyl chloride sec-butyl chloride, isobutyl chloride, chloroform, carbon tetrachloride, and the like. The most preferred solvent is methylene chloride which boils at about 40° C.

The amount of solvent can vary within a wide range. All that is required is that a solvent among be present. This will vary with the reactants and solvents used. In general, less of the chloroalkane solvents is required than hydrocarbon solvents since the chloroalkanes have higher solvent power. A useful solvent range is from about 50 to 500 parts per 100 parts of reactant. A preferred range is from 100 to 200 parts.

The reactants may generally be added in any manner to conduct the invention so long as an ether product is produced in the first step and the ether product is then reacted with the second phenol. Most generally, it is preferred to slowly add the first phenol of the invention to a mixture of the aldehyde and alcohol in a reaction container and reflux the reactant slowly. The reaction may be readily carried out by slowly adding the first phenol to the aldehyde and alcohol of the first step of the reaction using a secondary amine catalyst in solvent portions. This facilitates carrying out the first step of the invention to produce an ether in very high yield.

The diphenolic compounds formed by the present inventive process have less discoloration than bisphenols or other diphenolics formed by prior art processes. Furthermore, the present process produces a better yield of diphenolics than other prior art processes. Such prior art processes used strong base steps for coupling. Use of the strong bases like KOH resulted in yellowed or otherwide discolored product. The temperature of the second reaction step is fairly dependent upon the strength and concentration of the acid catalyst. A preferred strength of $H_2SO_4$ is 70-84%. If a lower concentration or weaker acid is used, a higher temperature may be required.

The invention will be better understood by reading of the following nonlimiting examples.

EXAMPLE 1

This example demonstrates a method of preparation of one of a variety of precursor ethers of the invention.

Methanol, 440 ml., 48 grams paraformaldehyde, and 6 grams of a 40 percent aqueous solution of dimethylamine are charged to a three-neck round bottom flask and refluxed (about 65° C.). A solution of 2,6-diisopropylphenol (178.28 grams—1 mole) in 100 ml. methanol is added dropwise over a period of more than two days. Seven gas chromatography (GC) analyses were taken at representative intervals. They indicated a slow but progressing reaction. After the first GC (one hour) 2.91 grams (0.024 mole) N-methyltoluidine were added. After the fourth GC (21 hours), 5.95 grams (0.05 mole) N-methyltoluidine, 24.87 grams (0.829 mole) paraformaldehyde, and 100 ml. methanol were added while the reaction continued. After 27 hours, 75 ml. methanol and 10.6 grams 40% dimethylamine were distilled off and the refluxing was then continued. At 45 hours, the seventh GC indicated 1.0 area percent 2,6-diisopropylphenol, 35.5 area percent 2,6-diisopropyl-α-methoxy-p-cresol; 5.3 area percent 2,6-diisopropyl-α,α-dimethoxy-p-cresol; and a small amount of 4,4'-bis(2,6-diisopropylphenol). The reaction product was slightly yellow-brownish in color. The solution was concentrated and the precipitated crystals were filtered and recrystallized from isooctane, given two methanol washings, and dried in vacuum. A GC analysis indicated 95 percent of the desired 2,6-diisopropyl-α-methoxy-p-cresol product which was dried in vacuum at room temperature. The yield was 57.4 grams having a melting point of 85.5–86.0. The solvent taken off still contained a large amount of product (very soluble in methanol) some of which precipitated. The residue after distilling off the solvent was crystallized from an oily dark red liquid and filtered off. After washing and recrystallization, another 85.6 grams product were obtained for a total yield of 143 grams (64.4 percent). The structure was confirmed by NMR and GC/mass spectroscopy.

EXAMPLE 2

The following example is a method of preparation of the compounds of the present invention from the precursor ether of Example 1.

Portionwise over a period of about two hours and 15 minutes, 122.54 grams (0.552 mole) of 2,6-diisopropyl-α-methoxy-p-cresol (an ether) was added to a mixture of 101.29 grams (0.829 mole) 2,6-dimethylphenol and 114.6 grams of 78 percent sulfuric acid in 690 ml. of methylene chloride. The reaction was carried out at atmospheric pressure and 4°–6° C. under a nitrogen atmosphere with mechanical stirring in a two liter three-neck flask. The temperature was maintained with an ice water bath. Immediately after the eighth of thirteen ether portions had been added, no ether could be detected by gas chromatography analysis (GC), indicating a very fast reaction. After the total addition of the ether, the reaction mixture was allowed to come to room temperature and a second GC indicated no ether present; 90.74 area percent of product phenol, 4-[[4-hydroxy-3,5-bis(1-methylethyl) phenyl]methyl]-2,6-dimethyl; and some dimethylphenol. The mixture was slightly pinkish to yellow-orange. The mixture was transferred to a separatory funnel and rinsed out of the flask with methylene chloride. The heavy sulfuric acid layer was drained off. Water was added and the mixture agitated. Additional methylene chloride was added followed by two 150 ml. water washes.

The methylene chloride and excess 2,6-dimethylphenol was distilled off under vacuum. The viscous liquid product was crystallized in 276 ml. isooctane using seed crystals from a previous run. The product was filtered and rinsed with 50 ml. cold isooctane. The product melting point was only 73°-75° C. and the yield was about 160 grams (above 93 percent).

EXAMPLE 3

The same general procedure of Example 2 was used herein. The reactants in the first step of the process of the invention in this example were 4.44 grams (0.02 mole) 2,6-diisopropyl-4-methoxy-para-cresol, 30 milliliters methylene chloride solvent, 3.34 grams of 70% H$_2$SO$_4$, and 3.67 grams (0.03 moles) 2,6-dimethylphenol. The ether was added portion wise (7 portions) over a period of about 1 hour at a temperature of about 4°-8° C. Only 2.34 grams of the acid were present in the starting reaction mixture of methylene chloride and 2,6-dimethylphenol. A gas chromatography analysis was made of the very slightly pink reaction mixture after the addition of the ether. Some starting material was apparently still present and the reaction mixture, which had warmed to room temperature, was again cooled to about 4° C. whereupon an additional 1.0 gram of 70% H$_2$SO$_4$ was added. The cooling bath was removed and after another hour when the reaction mixture had reached room temperature, a second gas chromatography analysis was made. After two more hours a third gas chromatography analysis was made and the reaction showed to be essentially completely. The reaction mixture was worked up in the usual manner using a separatory funnel and additional methylene chloride, draining off the acid. Water and sodium bicarbonate was added to raise the pH to about 6-7 and the solvent was distilled off with some excess 2,6-dimethylphenol. The next day, the residue was distilled in a Kugel-rohr up to about 106° C. The product was determined to be 92.6% pure by gas chromatography analysis. Gas chromatography mass spectroscopy and nuclear magnetic resonance spectroscopy confirmed the identity of the structure as

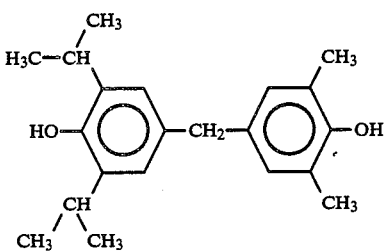

some starting material and a small portion of a dimer component were also present. The product was crystallized by petroleum ether at 30°-65° C. and from isooctane/cyclohexane. The product was again crystallized from 10 milliliters of isooctane and the melting point was determined at 73.5°-75.5° C. with very slightly yellow crystal. The product was again recrystallized from 15 milliliters of isooctane and dried in vacuum. The melting point was determined to be 75.3°-76° C. (yellow crystals). A total weight of 4.95 grams relatively pure product was provided. This is a yield of 79%.

EXAMPLE 4

In this example, 4.44 grams of 2,6-diisopropyl-paramethoxycresol was dissolved in 40 ml. methylene chloride and gradually added to a mixture of 3.67 grams 2,6-dimethylphenol and 4.67 grams 70% H$_2$SO$_4$ in 40 ml. methylene chloride. The reaction was carried out at about 5° C. and an additional 2 grams of 83.6% H$_2$SO$_4$ was added 10 minutes after the reaction had started. A first gas chromatography analysis at 40 minutes indicated that the reaction was proceeding fairly quickly with the slow addition of the ether. After 3 hours the ice bath was removed and the product was worked up in the usual fashion. The identity of the compound was again confirmed by several analytical techniques and 5.08 grams of product were obtained for a yield of 81.4%. The product was white instead of yellow as no sodium bicarbonate wash was used with the product. If the product is worked up without sodium bicarbonate, using only water instead, the product crystals are pure white.

Although a preferred embodiment of the best mode of the invention has been shown above, various features of the inventive process may be changed without departing from the scope or spirit of the invention as defined by the appended claims.

I claim:
1. A process for preparation of diphenolic compounds, said process comprising:
    (1) reacting in the presence of a catalytic amount of a secondary amine catalyst: an aldehyde, an alcohol, and a first phenol having exactly two of the three positions ortho and para to the hydroxyl group substituted and the other two meta positions optionally substituted with independently selected alkyl, cycloalkyl, aryl, alkaryl, aralkyl, halogen, or a group of the formula —(R″″)$_n$—CX$_3$ where R″″ is a divalent hydrocarbon preferably containing about one to twelve carbon atoms, n is zero or one, and X is halogen to form as the predominant product a hydroxybenzyl ether of said alcohol; and
    (2) reacting said ether product of step (1) in the presence of an acid catalyst with a second phenol having at least one position ortho or para to the hydroxyl group unsubstituted except for H.
2. The process of claim 1 wherein said alcohol is a lower alkanol.
3. The process of claim 2 wherein said lower alkanol is methanol present in excess of the stoichiometric amount required to make the ether of step 1.
4. The process of claim 3 wherein said alcohol is present in solvent quantities.
5. The process of claim 1 wherein said secondary amine is a dialkylamine or di-(hydroxyalkyl) amine.
6. The process of claim 5 wherein said secondary amine is dimethylamine.
7. The process of claim 1 wherein said aldehyde is selected from formaldehyde, acetaldehyde, benzalde- hyde, paraformaldehyde, crotonaldehyde, butyraldehyde, furfuraldehyde, glyoxalic acid, benzylaldehyde, and isobutyraldehyde.

8. The process of claim 7 wherein said aldehyde is formaldehyde or paraformaldehyde.

9. The process of claim 1 wherein said first phenol is a 2,6-dialkylphenol.

10. The process of claim 9 wherein said second phenol is a different 2,6-dialkylphenol.

11. A process for the production of a diphenolic compound, said process comprising the steps of:
  (1) reacting an alcohol, an aldehyde, and a first phenol having 2-4 like or different ring substituents selected from halogen, alkyl, cycloalkyl, aryl, aralkyl, alkaryl, or a group of the formula —(R''''-)$_n$—CX$_3$ where R'''' is a divalent hydrocarbon preferably containing about 1-12 carbon atoms, n is 0 or 1, and X is halogen, said first phenol having only one position ortho or para to the hydroxyl group unsubstituted except for H, in the presence of a secondary amine to form as the predominant product an ether intermediate; and
  (2) reacting the ether intermediate from step (1) with a second phenol having 0-4 like or different ring substituents selected from halogen, alkyl, cycloalkyl, aryl, alkaryl, aralkyl, or a group of the formula —(R'''')$_n$—CX$_3$ where R'''' is a divalent hydrocarbon preferably containing about 1-12 carbon atoms, n is 0 or 1 and X is halogen wherein said second phenol has at least one position ortho or para to the hydroxyl group unsubstituted except for H in the presence of an acid catalyst.

12. The process of claim 11 wherein step (1) is carried out at a temperature sufficient to provide reflux of the reaction mixture.

13. The process of claim 12 wherein the first phenol is gradually added to the other reactants and catalysts and the secondary amine.

14. The process of claim 12 wherein said first step is carried out at about 50°-100° C.

15. The process of claim 11 wherein the second step is carried out at about 0°-35° C.

16. The process of claim 15 wherein the second step is carried out at about 0°-10° C.

17. The process of claim 11 wherein the acid catalyst of the second step is sulfuric acid.

18. A process for the production of divalent-hydrocarbon-bridged diphenolic compounds of structures I, II, III, or IV:

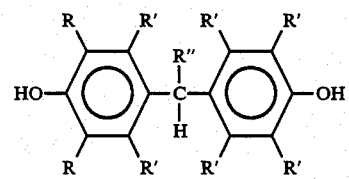

(I)

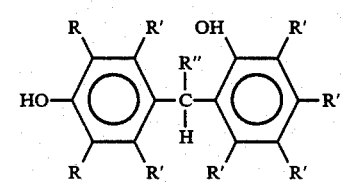

(II)

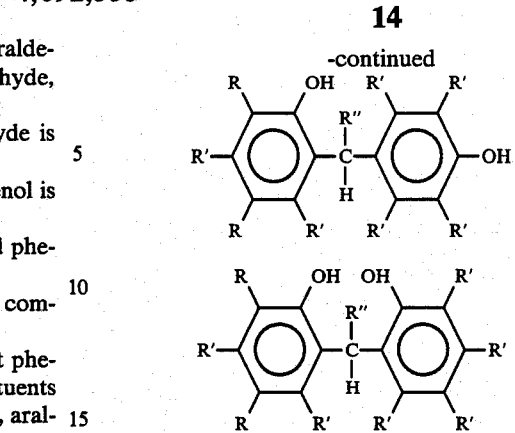

wherein the R are independently selected from the group consisting of alkyl, cycloalkyl, aromatic, halogen, or a group of the formula —(R'''')$_n$—CX$_3$ wherein R'''' is a divalent hydrocarbon preferably of 1-12 carbon atoms, n is 0 or 1, and X is halogen; wherein the R' are independently selected from H and the same group as the R; and wherein R'' is selected from H or alkyl, cycloaliphatic, alkenyl, aromatic, heteroatomic, or heterocyclic radicals; said process comprising reacting a phenol of structure A or B:

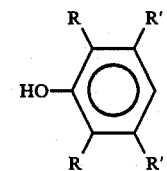

(A)

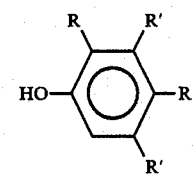

(B)

wherein the R and R' are as defined above, with an alcohol of structure R'''—OH wherein R''' is a monovalent hydrocarbon and an aldehyde of structure R''CHO wherein R'' is as defined above, in the presence of a secondary amine to form as the predominant product an ether intermediate of structure C or D:

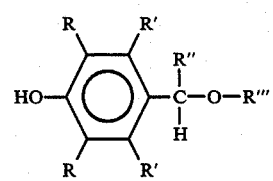

(C)

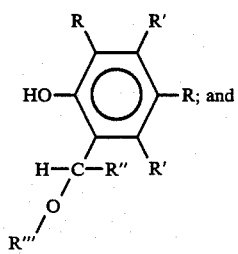

(D)

reacting said ether intermediate with a phenol of structure E or F:

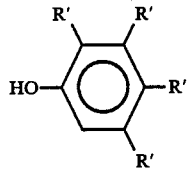 (E)

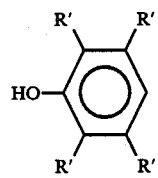 (F)

wherein the R' are as defined above, in the presence of an acid catalyst.

19. The process of claim 18 wherein the first step is carried out at about the reflux temperature of the alcohol.

20. The process of claim 18 or 19 wherein the second step is carried out at 0°–35° C.

21. The process of claim 18 wherein said phenol of structure A or B is gradually added to the alcohol, aldehyde, and secondary amine.

22. The process of claim 18 wherein said acid is $H_2SO_4$.

23. A process comprising the steps of:
(1) reacting a phenol of structure:

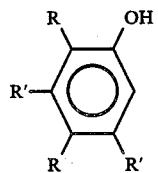

wherein the R are independently selected from the group consisting of alkyl, cycloalkyl, aromatic, halogen, and a radical of the formula —(R'''')$_n$—CX$_3$ wherein R'''' is a divalent hydrocarbon preferably of 1-12 carbon atoms, n is 0 or 1, and X is halogen and wherein the R' are independently selected from H and the members of the same group as R, with an alcohol of structure R'''—OH wherein R''' is a monovalent hydrocarbon and an aldehyde of structure R''CHO wherein R'' is H or an alkyl, cycloaliphatic, alkenyl, aromatic, heteroatomic, or heterocyclic radical, in the presence of a secondary amine; and (2) forming as the primary product an ether of structure:

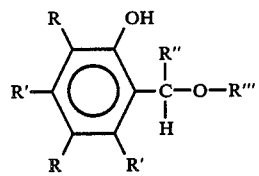

24. The process of claim 23 further comprising reacting said ether formed in step (2) with a phenol of structure:

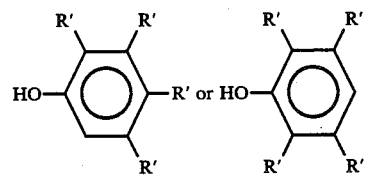

wherein the R' are as defined above, in the presence of an acid catalyst and forming as the primary product an undiscolored divalent-hydrocarbon-bridged diphenolic compound of structure:

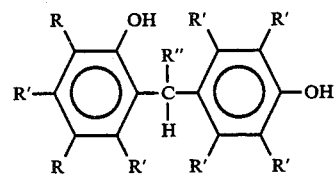

or

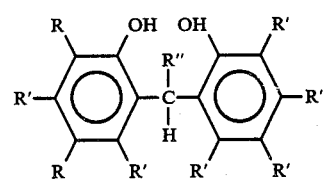

25. A process for preparing an unsymmetrical diphenolic compound, said process comprising the steps of:
(1) reacting at a temperature of up to about 150° C., in the presence of a catalytic amount of a secondary amine catalyst: an aldehyde, an alcohol, and a first phenol having one lower alkyl substituent ortho to the hydroxyl group of the first phenol and one lower alkyl substituent ortho or para to the hydroxyl group of the first phenol to form as the predominant product a di-loweralkyl-4-hydroxybenzyl ether of said alcohol; and
(2) reacting said di-loweralkyl-4-hydroxybenzyl ether in the presence of an acid catalyst with a second, different phenol having at least one lower alkyl substituent ortho or para to the hydroxyl group of the second phenol to form as the predominant product an unsymmetrical diphenolic compound.

* * * * *

UNITED STATES PATENT AND TRADEMARK OFFICE
CERTIFICATE OF CORRECTION

PATENT NO. : 4,692,555
DATED : SEPTEMBER 8, 1987
INVENTOR(S) : KJU H. SHIN

It is certified that error appears in the above-identified patent and that said Letters Patent is hereby corrected as shown below:

Column 1 line 26 reads "April 9 to Shin" and should read
-- April 9, 1984 to Shin -- .

Column 4 line 68 reads "and D:" and should read -- or D: -- .

Column 6 line 44 reads "alkys" and should read -- alkyls -- .

Column 7 line 51 reads "are most preferred" and should read
-- are more preferred -- .

Column 9 line 41 reads "chloride sec-butyl" and should read
-- chloride, sec-butyl -- .

Column 9 line 46 reads "solvent among be" and should read
-- solvent amount be -- .

Column 11 line 19 reads "(above 93 percent)" and should read
-- (about 93 percent) -- .

Column 11 line 42 reads "essentially completely" and should read
-- essentially complete -- .

Signed and Sealed this

Twelfth Day of January, 1988

Attest:

DONALD J. QUIGG

Attesting Officer

Commissioner of Patents and Trademarks